(12) United States Patent
McRuer et al.

(10) Patent No.: US 10,996,213 B2
(45) Date of Patent: May 4, 2021

(54) MOLECULAR ANALYSIS SYSTEM WITH WELL ARRAY

(71) Applicant: Stratos Genomics, Inc., Seattle, WA (US)

(72) Inventors: Robert N. McRuer, Mercer Island, WA (US); Steven Hickman, Seattle, WA (US)

(73) Assignee: STRATOS GENOMICS, INC., Seattle, WA (US)

( * ) Notice: Subject to any disclaimer, the term of this patent is extended or adjusted under 35 U.S.C. 154(b) by 126 days.

(21) Appl. No.: 16/069,693

(22) PCT Filed: Jan. 12, 2017

(86) PCT No.: PCT/US2017/013162
§ 371 (c)(1),
(2) Date: Jul. 12, 2018

(87) PCT Pub. No.: WO2017/123737
PCT Pub. Date: Jul. 20, 2017

(65) Prior Publication Data
US 2019/0011424 A1 Jan. 10, 2019

Related U.S. Application Data

(60) Provisional application No. 62/277,873, filed on Jan. 12, 2016.

(51) Int. Cl.
| | |
|---|---|
| *G01N 27/403* | (2006.01) |
| *G01N 33/487* | (2006.01) |
| *B01L 3/00* | (2006.01) |
| *G01N 33/483* | (2006.01) |
| *G01N 27/327* | (2006.01) |

(52) U.S. Cl.
CPC ...... *G01N 33/48721* (2013.01); *B01L 3/5085* (2013.01); *B01L 3/502715* (2013.01); *G01N 33/4836* (2013.01); *B01L 3/50853* (2013.01); *B01L 2200/12* (2013.01);
(Continued)

(58) Field of Classification Search
CPC .............. G01N 33/48721; G01N 33/4836
See application file for complete search history.

(56) References Cited

U.S. PATENT DOCUMENTS 6,051,380 A * 4/2000 Sosnowski ........... B01J 19/0046
435/6.11
6,942,554 B1 * 9/2005 Mandina ................... B24B 1/04
451/159
(Continued)

FOREIGN PATENT DOCUMENTS

WO 2010/117470 A2 10/2010

OTHER PUBLICATIONS

Saha et al., "Scalable micro-cavity biliayer lipid membrane arrays for parallel ion channel recording," Sensors and Actuators B 199 (2014) 76-82 (Year: 2014).*
(Continued)

*Primary Examiner* — Alexander S Noguerola
(74) *Attorney, Agent, or Firm* — Seed IP Law Group LLP

(57) ABSTRACT

Nanopore-based molecular analysis systems including a disposable well array, methods of analysis of biomolecules using nanopore molecular analysis systems, and methods of fabricating disposable well arrays are provided.

25 Claims, 11 Drawing Sheets

(52) U.S. Cl.
CPC .............. *B01L 2300/0645* (2013.01); *B01L 2300/0819* (2013.01); *B01L 2300/0893* (2013.01)

(56) References Cited

U.S. PATENT DOCUMENTS

| | | | |
|---|---|---|---|
| 2014/0034497 A1* | 2/2014 | Davis | G01N 27/44791 204/451 |
| 2014/0062503 A1* | 3/2014 | Behrends | G01R 27/00 324/649 |

OTHER PUBLICATIONS

Stöhr et al., "High-resolution permanent photoresist laminate for microsystem, applications," J. Micro/Nanolith. MEMS MOEMS 7(3), 033009 (Jul.-Sep. 2008) (Year: 2008).*

Compliant Pin Description definition on http://www.interfacebus.com/glossary-pwb-compliant-pin-description.html downoaded Jul. 1, 2020 (last modifed Apr. 1, 2012) (Year: 2012).*

\* cited by examiner

<<Prior Art>>

300

MOLECULAR ANALYSIS SYSTEM WITH WELL ARRAY

BACKGROUND

Technical Field

The present invention is generally related to improved biomolecular measurement, and more particularly to nanopore-based molecular analysis systems including a disposable well array, methods of analysis of biomolecules using nanopore molecular analysis systems, and methods of fabricating disposable well arrays.

Description of the Related Art

Measurement of biomolecules is the foundation of modern medicine and is used not only in both diagnostics and therapy, but also in drug development and, more broadly, medical research. Nucleic acids encode the necessary information for living things to function and reproduce, and are essentially a blueprint for life. Determining such sequences is therefore a tool useful in pure research into how and where organisms live, as well as in applied sciences, such as drug development. In medicine, sequencing tools can be used for diagnosis and to develop treatments for a variety of pathologies, including cancer, heart disease, autoimmune disorders, multiple sclerosis, and obesity. In industry, sequencing can be used to design improved enzymatic processes or synthetic organisms. In biology, such tools can be used to study the health of ecosystems, for example, and thus have a broad range of utility. Similarly, measurement of proteins and other biomolecules have provided markers and understanding of disease and pathogenic propagation.

An individual's unique DNA sequence provides valuable information concerning their susceptibility to certain diseases and provides patients with the opportunity to screen for early detection and to receive preventative treatment. Furthermore, given a patient's individual genetic blueprint, clinicians would be capable of administering personalized therapy to maximize drug efficacy and to minimize the risk of an adverse drug response. Similarly, determining the genetic blueprint of pathogenic organisms could lead to new treatments for infectious diseases and more robust pathogen surveillance. Low cost, whole genome DNA sequencing will therefore provide the foundation for modern medicine. To achieve this goal, sequencing technologies must continue to advance with respect to throughput, accuracy, and read length.

Over the last decade, a multitude of next generation DNA sequencing technologies have become commercially available that have dramatically reduced the cost of sequencing whole genomes. These include sequencing by synthesis ("SBS") platforms, such as those developed by Ilumina, Inc., 454 Life Sciences, Ion Torrent, and Pacific Biosciences, and analogous ligation based platforms, such as those developed by Complete Genomics and Life Technologies Corporation. A number of other technologies are in development that utilize a wide variety of sample processing and detection methods. For example, GnuBIO, Inc. uses picoliter reaction vessels to control millions of discreet probe sequencing reactions, whereas Halcyon Molecular is developing technology for direct DNA measurement using a transmission electron microscope.

Nanopore-based nucleic acid sequencing is a compelling approach that has been widely studied. Pioneering studies by Kasianowicz et al. (Proc. Natl. Acad. Sci. USA. 93: 13770-3, 1996) characterized single-stranded polynucleotides as they were electrically translocated through an alpha hemolysin nanopore embedded in a lipid bilayer. It was demonstrated that during polynucleotide translocation partial blockage of the nanopore aperture could be measured as a decrease in ionic current. However, polynucleotide sequencing in nanopores is burdened by having to resolve tightly spaced bases (0.34 nm) with small signal differences immersed in significant background noise. The measurement challenge of single base resolution in a nanopore is made more demanding due to the rapid translocation rates observed for polynucleotides, which are typically on the order of 1 base per microsecond. Translocation rate can be reduced by adjusting run parameters such as voltage, salt composition, pH, temperature, and viscosity, to name a few. However, such adjustments have been unable to reduce translocation rate to a level that will allow for single base resolution.

Several strategies have been employed to overcome the technical challenges of nanopore-based nucleic acid sequencing. For example, Stratos Genomics is developing a method called Sequencing by Expansion ("SBX") that uses a biochemical process to transcribe the sequence of a DNA onto a measurable polymer called an "Xpandomer" (Kokoris et al., U.S. Pat. No. 7,939,259, High Throughput Nucleic Acid Sequencing by Expansion). The transcribed sequence is encoded along the Xpandomer backbone in high signal-to-noise reporters that are separated by ~10 nm and are designed for high-signal-to-noise, well-differentiated responses. These differences provide significant performance enhancements in sequence read efficiency and accuracy of Xpandomers relative to native DNA. Xpandomers can enable several next generation DNA sequencing detection technologies, and are well suited to nanopore sequencing.

In another approach, Oxford Nanopore Technologies (Oxford, United Kingdom) has developed a direct sequencing technique for nanopores that uses enzymes to control DNA translocation rate. The measured signals are determined by the composite blockages of 3 or 4 sequential bases as the DNA is ratchetted through the nanopore. Individual base identities are deconvolved from these signals.

At present, commercial availability of nanopore-based nucleic acid sequencing systems is limited. Oxford Nanopore Technologies has marketed a compact nanopore DNA sequencer, called the Minion, which couples a flow cell to a 512 nanopore well array with an integrated CMOS amplifier array. Genia Technologies (Santa Clara, Calif., USA) is developing similar nanopore amplifier arrays in CMOS for DNA sequencing applications. In both these examples, the entire sequencing systems, including the flow cells and CMOS chips, are considered disposable.

In the semiconductor industry, improved performance of interchip connections has led to development of through silicon vias (TSV) that allows silicon chips to be stacked in a 3D architecture (see, e.g., P. S. Andry, Fabrication and characterization of robust through-silicon vias for silicon-carrier applications, IBM Journal of Research and Development, vol. 52, no. 6, pp. 571-581, November 2008). The TSV is a via that passes through the thickness of the silicon chip to create a contact on the bottom of the chip that can bond directly to contacts on the top of another chip. These vias are drilled using deep silicon dry etching technology such as Bosch etching (see, e.g., U.S. Pat. No. 5,501,893), which can create holes with aspect ratios of 20 or more (i.e., where the hole depth is 20 times its diameter. For example, 15 μm diameter holes drilled through a 300 μm silicon substrate). The holes are then insulated with silicon oxide such as a thermally grown oxide or a deposited oxide. Next, they are filled with metal, typically by seeding a metal conductor and then electroplating with copper. The surfaces are then chemically polished and metallized appropriately to form the contacts.

Another technology is through glass via (TGV) that uses thin glass substrates 25 to 100 um in thickness. This glass can be purchased in meter-wide rolls and is sold to the flat panel display industry (Schott and Corning). Methods have been developed to fabricate dense arrays of high aspect holes in thin glass (see, e.g., U.S. Published Patent Application No. 2014/0217075 to Asahi Glass Company Ltd.).

Despite the advances that have been made in this field, there remains a need for new and improved well arrays for making biomolecular measurements, as well as a need for methods and products related thereto. The present invention fulfills these needs, and provides further related advantages as evident up reference to the following description and attached drawings.

BRIEF SUMMARY

Briefly stated, embodiments of this disclosure include nanopore-based molecular analysis systems and methods of fabricating components of nanopore-based molecular analysis systems.

In one embodiment, a high density array of microwells in provided comprising a substrate, wherein the substrate comprises a plurality of microwells, wherein the dimension of each of the microwells is defined by a high aspect ratio; a plurality of electrodes, wherein a single electrode is disposed in each of the plurality of microwells; and a plurality of connectors, wherein each of the connectors is in electrical communication with a microwell.

In more specific embodiments, the high aspect ratio of the microwells is greater than or equal to a height to diameter ratio of about 5, or is greater than or equal to a height to diameter ratio of about 10, or is greater than or equal to a height to diameter ratio of about 15.

In more specific embodiments, each of the microwells has a depth that is at least about half the thickness of the substrate.

In more specific embodiments, the substrate has a thickness of about 300 μm and each of the microwells has a diameter of about 20 μm and a depth of up to about 300 μm.

In more specific embodiments, each of the plurality of electrodes has a surface area that covers greater than 25 percent of the interior of the walls of the microwell in which it is disposed, or covers greater than 50 percent of the interior of the walls of the microwell in which it is disposed, or covers substantially 100 percent of the interior of the walls of the microwell in which it is disposed.

In more specific embodiments, the density of the microwells is greater than about 10,000 per $cm^2$, or greater than about 50,000 per $cm^2$, or is up to at least 100,000 per $cm^2$.

In more specific embodiments, the substrate is silicon or glass.

In more specific embodiments, each of the connectors are compliant. In a further embodiment, the compliant connectors include a PEDOT polymers or a hybrid polymer including a conductive material. In a further embodiment, each of the connectors includes a non-conductive compliant polymer coated with a metal.

In another embodiment, a device is provided for determining nucleic acid sequence information, the device comprising a high density array of microwells; a semiconductor chip in reversible electrical communication with the high density array; and an upper fluidic region in fluidic communication with the high density array.

In more specific embodiments, the high density array and the upper fluidic region are disposable and the semiconductor chip is reusable.

In more specific embodiments, one or more of the connectors of the array are compliant and form the electrical communication with the semiconductor chip. In further embodiments, the compliant connectors include a PEDOT polymers or a hybrid polymer including a conductive material. In further embodiments, the compliant connectors include a non-conductive polymer coated with a metal.

In another embodiment, a method of fabricating a high density array of microwells in a substrate is provided, comprising the step of deep silicon etching.

In another embodiment, a method of fabricating a high density array of microwells is provided, comprising steps of providing a substrate and applying a layer of silicon oxide and a layer of silicon nitride on a first surface of the substrate; forming a plurality of microwells originating from a second surface of the substrate and ending in substantial proximity to the first surface of the substrate; applying an insulating layer of thermal oxide to the interior surfaces of the microwells; applying a conductive seed layer to the interior wall and bottom surfaces of the microwells; spin coating a layer of conductive compliant polymer over the second surface of the substrate, wherein the polymer layer seals the openings of the wells; etching the polymer over the second surface to form compliant conductive interconnects; etching the first surface of the substrate to form microwell apertures; and electroplating the microwells with metal to form a cylindrical electrode in each microwell, wherein the surface area of the electrode is substantially similar to the surface area of the microwell.

BRIEF DESCRIPTION OF THE SEVERAL VIEWS OF THE DRAWINGS

In the figures, the sizes and relative positions of elements are not necessarily drawn to scale and some of these elements are arbitrarily enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
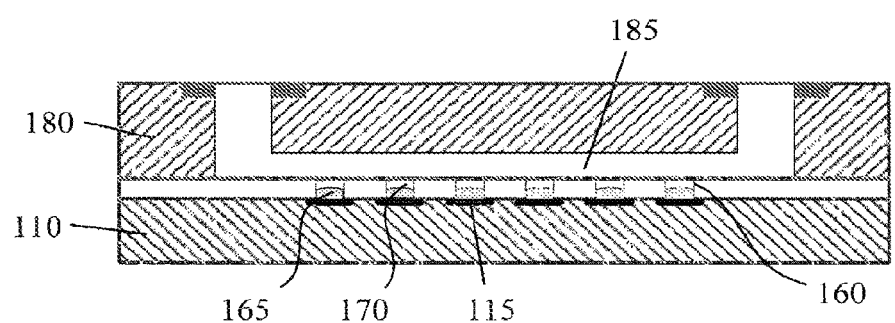
FIG. 1 is a schematic depicting a cross-sectional view of a conventional nanopore-based molecular analysis system.

It is to be understood that the terminology used herein is for the purpose of describing specific embodiments only and is not intended to be limiting. It is further to be understood that unless specifically defined herein, the terminology used is to be given its traditional meaning as known in the relevant art. Further, any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used herein, the terms "about" and "around" are used synonymously and mean±20% of the indicated value. In more specific embodiments, these terms mean plus or minus (±) 10% of the indicated value, and in still more specific embodiments mean±5% of the indicated value.

As used herein, the term "substantially" means to a significant extent, and in the context of a number value corresponds to within 5% of the indicated range, value or structure. In more specific embodiments, the term "substantially" means, in the context of a number value to be within 2%, and in still more specific embodiments mean within 1%, of the indicated range, value or structure.

In one embodiment, the invention described herein takes advantage of TSV/TGV development and applies these fabrication technologies to create deep well arrays in a disposable substrate that is used as a component of a nanopore molecular analysis system. The deep well arrays of the present invention improve performance and reduce cost of nanopore arrays based upon CMOS amplifier arrays. The disposable intermediary substrate of the present invention provides a high density of deep wells that makes a temporarily interconnect to the CMOS amplifier array. Instead of requiring disposal of the high value CMOS chip after use, the system of the present invention offers the advantage of providing a reusable CMOS chip, with the intermediary substrate being the sole disposable.

As described in greater detail herein, nanopore-based molecular analysis systems and methods of fabricating nanopore-based molecular analysis systems are provided. By way of example, some embodiments provide nanopore-based molecular analysis systems capable for applications requiring high throughput molecular analysis, such as human genome sequencing. The nanopore-based molecular analysis systems of the present invention include a disposable well array (DWA), used to support a high density array of nanopores. In this embodiment, the wells of the array each have a large height-to-width ratio that maximizes well volume, while enabling high overall well density in the array. The disposable well array also includes a corresponding contact array, which forms electrical connections (i.e. "interconnections") between each well in the DWA and an amplifier in a semiconductor sensor chip, herein referred to as a CMOS amplifier array. The high density connections between the DWA and the CMOS amplifier array are temporary by design and therefore may be broken and reformed as multiple DWAs are used, then replaced, on a single, reusable CMOS array.

For genome sequencing, nanopore-based molecular analysis systems often function by passing a single-stranded DNA (ssDNA) polymer through a pore of nanometer scale and monitoring the modulation of the ion current passing through the nanopore. Typically, the nanopore is designed to have a size that allows the nucleic acid polymers to pass only in a sequential, single file order. As the polymer molecule passes through the nanopore, differences in the chemical and physical properties of the monomeric units that make up the polymer, e.g., the nucleotides that compose the ssDNA, are translated into characteristic ion current signals. These signals are read by an external amplifier circuit built with electrodes places in the electrolyte on each side of the nanopore.

FIG. 1 illustrates the general features of a molecular analysis system 100 based upon biological nanopores, also referred to here as a CMOS nanopore sequencing device. Nanopore sensor interfaced with CMOS technology have been described, e.g., in Magierowski, S. M., Huang, Y., Wang, C., and Ghafar-Zadeh, E. Nanopore-CMOS Interfaces for DNA Sequencing. Biosensors 6 (42) (2016). Standard CMOS processing is used to fabricate an array 110 of hundreds or thousands of electronic amplifiers 115. The CMOS amplifier arrays are then post-processed to form well structures 160 over each amplifier using lithographically defined coatings. Ion sensitive electrodes 165, such as silver/silver chloride (Ag/AgCl) electrodes, are formed in the wells and connect to the corresponding amplifiers. A flow cell 180 is bonded with the CMOS well array to provide fluid access to the wells. A sequence of processing steps are performed by passing fluids through the flow channel 185 to fill the wells with electrolyte and form a lipid bilayer across each well aperture which electrically isolates the wells from the flow channel and each other. Next, a biological nanopore is inserted into each bilayer to electrically connect the flow channel (i.e. cis reservoir 185) to each well reservoir (i.e.

trans reservoir 170). Electrolyte ions are the charge carriers which conduct current through the nanopore. This integrated CMOS/flow channel structure 100 is, by design, a single-use device, due to the limited lifetime of the electrodes and flow channel/well contamination.

For whole genome DNA sequencing applications using nanopore-based molecular analysis systems, high read rates are necessary to provide thorough and accurate sequence information in an acceptable time period. For example, to sequence 6 billion bases of the human genome at 20× coverage in 4 hours, an average throughput of over 8 million bases per second is required. For a nanopore-based system, over 80,000 individual functional nanopores would be required, even assuming high average base read rates approaching 100 bases per second. Thus, for a disposable nanopore analysis system, the well array must be dense. However, the individual wells must also be large enough to provide sufficient operational lifetime of the electrode and to mitigate against ion concentration depletion (or accumulation), as further discussed below.

Figure 2:
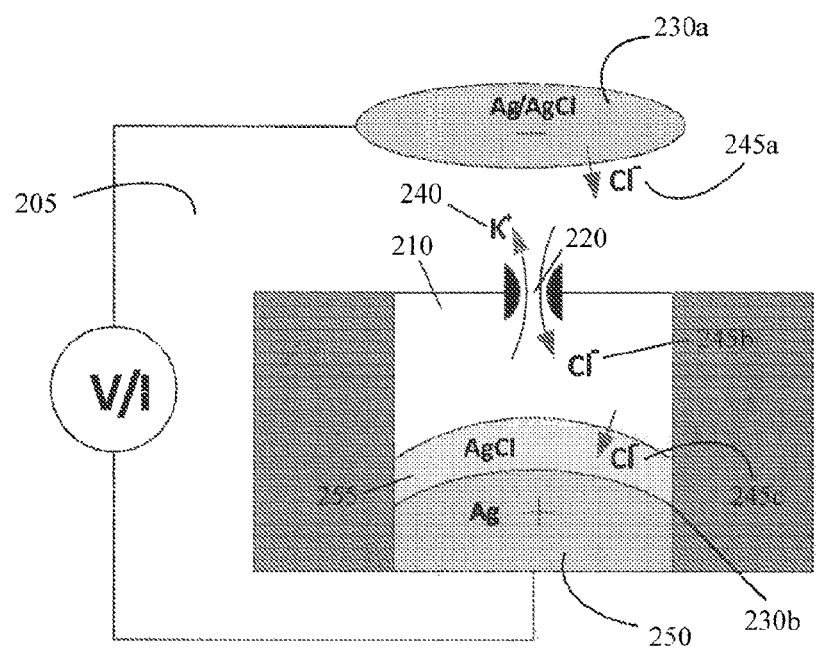
FIG. 2 is a cartoon summarizing the processes of electrode and ion concentration depletion.

Electrode and ion concentration depletion, which limit operational lifetime of wells in nanopore sequencing systems, is further discussed with reference to FIG. 2. FIG. 2 illustrates a simplified nanopore-based device 200, which includes a cis reservoir 205, a well (or trans reservoir) 210, a nanopore 220, and Ag/AgCl electrodes 230a and 230b. Current passes through electrode 230b when a reaction of the ion charge carrier at its surface releases or captures an electron. Generally, the electrode will eventually lose its conductivity due to this reaction, by exhausting the reactants in the electrode or electrolyte or by formation of insulating products that prevent efficient charge transfer. For example, Ag/AgCl cathode 230b in KCl electrolyte will eventually covert its silver 250 to silver chloride 255 until the free silver is exhausted or inaccessible. In a small well volume that must contain the electrode, such as wells 160 of the CMOS nanopore sequencing device depicted in FIG. 1, this can be limiting. For example, a small silver disk electrode that is 1 μm thick and 10 μm in diameter has sufficient silver to sustain a 100 pA current for only 2 hours. However, conductivity may be reduced before this time limit as reaction kinetics are impeded with the buildup of AgCl reaction product 255 on the electrode surface. To increase electrode life, electrode volume and surface area in the well can be increased, however this has the disadvantage of further reducing electrolyte volume in the well.

Another consideration of small well reservoirs is the necessarily small electrolyte volume, which can lead to ion concentration depletion. Ion concentration depletion results from a nanopore translocation current that is due to an ion species that is not exchanged on the ion selective electrodes. This process is outlined with further reference to FIG. 2. With KCL electrolyte, a positive relative potential applied to the well (trans) electrode 230b will drive Cl⁻ ions 245a off the cis electrode 230a and onto well electrode 230b. The charge imbalance in the reservoirs can be satisfied by Cl⁻ ions 245b passing through nanopore 220 from cis to trans reservoirs or by K⁺ ions 240 passing through the nanopore from trans to cis reservoirs. The K⁺ ion translocation current will deplete the ion concentration of the small trans reservoir until a concentration gradient between the two reservoirs is sufficient to stop any net K⁺ ion current.

The relationship between ion flow, applied potential and concentration gradient can be modeled with Goldman's equation. Assuming typical values of mobility for an initial 1.0 M KCL electrolyte in a nanopore system with a single wild type alpha hemolysin inserted, well concentration depletion over time can be computed. For example, at 100 mV applied potential, a well reservoir that is 10 μm diameter by 10 μm deep will deplete its KCl concentration to 50% in less than 30 minutes. The rate of concentration depletion is inversely related to volume so, by comparison, a larger well with size 20 μm diameter by 100 μm deep loses less than 10% of its concentration in over 2 hours.

A solution to increase electrode operational lifetime, decrease electrode resistance, and reduce the rate of electrolyte concentration depletion is to increase well volume. However, as discussed above, an efficient nanopore-based sequencing system must also have a high density of wells. To maintain high well density while maximizing well volume, the most significant increase that can be made is to increase the depth of the wells. To achieve such well dimensions requires a fabrication process that can generate high aspect wells. There is no practical process to accomplish this on a CMOS amplifier array substrate using conventional lithography-based methods.

The present invention addresses the problem of limited well lifespan in a high density nanopore array by providing a modular molecular analysis system based on a dense well array in which high aspect wells are etched into a separate substrate that is not integral to the CMOS amplifier array. The high aspect wells enable high well density to be balanced with high well volume. The high volume wells increase the well electrode lifespan in terms of electrode life and buffer against the ion concentration depletion effect. In addition, multiple dense well array substrates may be sequentially used with a single reusable CMOS amplifier array, which avoids the high cost of replacing the CMOS chip, as required by conventional designs. This advantageously provides economic freedom to invest in larger CMOS substrates, which provides for either larger arrays or even larger volume wells (with larger area per CMOS amplifier).

Figure 3:
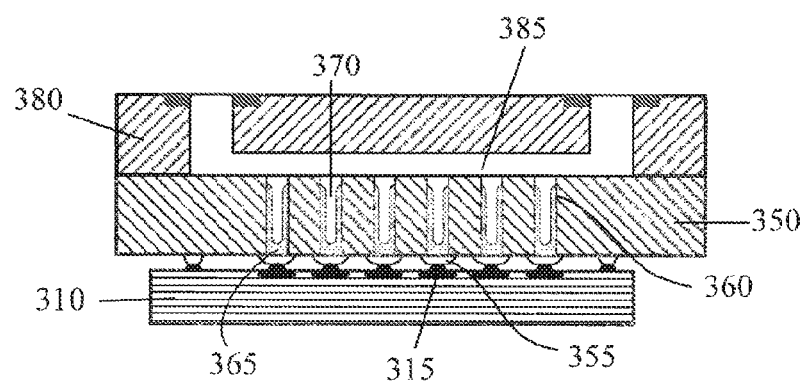
FIG. 3 is a schematic depicting a cross-sectional view of one embodiment of the invention.

FIG. 3 illustrates a cross-sectional view of a portion of an exemplary nanopore-based molecular analysis system 300 of the present invention with modular organization, which may function as a device for determining nucleic acid sequence information. The components of the system include a reusable CMOS amplifier array 310 that is in electrical communication with a disposable well array 350, which may also be referred to as an "intermediary substrate", "high density array of microwells", or "dense well array" and for simplicity, referred to herein as a "DWA". In contrast to the conventional CMOS array illustrated in FIG. 1, the wells of DWA 350 are formed in a separate substrate as it is not practical to form deep wells directly on the high-value CMOS substrate. DWA 350 is in fluid communication with a flow cell channel 385 located in the flow cell 380 that allows management of the microfluidic functions of the analysis system. The molecular analysis system of the present invention provides several further improvements over conventional systems, which may include, but are not limited to: i) a dense array of through substrate (high aspect) wells 360 capable of retaining relatively high volumes of electrolyte buffer 370; ii) high surface area electrodes 365 in each well; iii) compliant well contacts 355 under each well; and iv) temporary interconnects between compliant well contacts and cohort contacts 315 on the CMOS amplifier array.

The geometry of the wells 360 of the DWA intermediary substrate 350 is distinguished by a high aspect ratio, in which the ratio of the height of the well to the diameter of the well is greater than that of conventional array wells. Thus, the wells may be referred to as "high aspect wells". In some embodiments, the ratio of the height of the wells to the diameter of the wells is about five or greater. In other embodiments, the ratio of the height of the wells to the diameter of the wells is from about five to about ten. In other embodiments, the ratio of the height of the wells to the diameter of the wells may be about five, about six, about seven, about eight, about nine, or about ten. In yet other embodiments, the ratio of the height of the wells to the diameter of the wells is greater than ten or greater than twenty.

The high aspect wells of the DWA of the present invention may also be described as "through substrate", indicating that they penetrate into and through the substrate. This feature differs from conventional wells, which are formed on the surface of a CMOS substrate using standard lithographically applied coatings. The present invention makes use of distinct fabrication technologies to create the through substrate wells, as further described herein. In some embodiments, the depth of the wells is at least around half the thickness of the substrate. In other embodiments, the depth of the wells is greater than around half the thickness of the substrate. In one particular embodiment, the substrate has a thickness of around 300 µm, and each of the microwells has a depth of up to around 300 µm and a diameter of around 20 µm.

The geometry of the high aspect wells of the DWAs of the present invention maximizes well volume by increasing well depth. This enables the diameter of the wells to be minimized which, in turn, enables the density of the wells in the substrate to be increased. In some embodiments, the DWA provides a high density plurality of wells of greater than around 10,000 wells per cm$^2$. In other embodiments, the high density plurality of wells is greater than around 50,000 wells per cm$^2$. In other embodiments, the high density plurality of wells is greater than around 100,000 wells per cm$^2$. In other embodiments, the high density plurality of wells is greater than around 200,000 wells per cm$^2$.

Suitable substrates for fabrication of the DWAs of the present invention will be well known to those of skill in the art. In some embodiments, suitable substrates include silicon and glass.

Electrodes 365 of the DWA (i.e. the "trans" electrodes) are formed to maximize the surface area of the electrode in order to increase operational lifespan. By maximizing the surface area of the electrode, the thickness of the redox product that builds up on the surface of the electrode during use is reduced. For example, with Ag/AgCl electrodes, conductivity in a chlorine-based electrolyte is often limited at the electrode surfaces where the redox reaction, $Ag^+ + Cl^- \leftrightarrow AgCl$ occurs. The chlorinated electrode has an insulating layer of AgCl that coats the underlying Ag metal, thus for the reaction to proceed, the ions must diffuse between the metal and electrolyte through limited access channels. If this is a positive electrode, the AgCl layer thickens and ion diffusion is further constrained and the electrical resistance can increase until it is no longer acceptable. This limiting amount of AgCl growth delineates the amount of usable silver and how thick the silver plating should be.

In one embodiment, each well electrode substantially coats the entire surface of the interior of the wells in which it is disposed. The thickness of this coating can be chosen to provide a volume of electrode material sufficient for the application but also not so thick as to limit the electrolyte volume in the well. In some embodiments, the electrode surface area is the area of the interior well area adjusted for the thickness of the electrode coating. In other embodiments, the electrode surface area is greater than this area due to irregular surface topography. In other embodiments, the electrode surface area is less than the interior well surface area due to incomplete coverage of the well surface. The shape of the electrodes in any of these embodiments may be referred to as a "hollow cylinder" where the electrode covers the some (e.g. greater than 25%), most (e.g. greater than 50%) or all (e.g. substantially 100%) of the interior well walls. This hollow cylinder electrode shape offers a superior ratio of surface area to electrode metal volume as compared to an electrode located only at the bottom of the well. In another embodiment, geometries of the electrodes as described herein may be attained by depositing a seed layer of metal or other conductive material on part or all of the interior walls of the wells, followed by electroplating metal, such as silver, cylindrically along the interior walls of the wells to the desired final thickness. This seed layer may be formed by sputter deposition, atomic layer deposition, or electroless plating.

In addition to the trans electrodes, counter-electrodes (i.e. "drive" or "cis" electrodes) may be fabricated on the DWA device. In one embodiment, one or more of the DWA wells are used as counter-electrodes in which case they are not covered with a lipid membrane and thus are always in electrical contact with the conductive fluid in the flow cell channel. In this embodiment, the counter-electrodes are connected to the CMOS amplifier array in the same way as the lipid covered wells. In one embodiment each CMOS amplifier can be switched to be function as either a counter-electrode or well electrode. In other embodiments, the counter-electrodes are fabricated on the top surface of the DWA intermediary substrate or on the walls of the fluid channels in the flow cell as described with reference to FIG. 3), or in a combination of these methods.

Typically, the conducting material of the electrodes will be silver.

The array of well contacts 355 of the DWA is characterized by individual contacts of a small size and high overall density. Therefore, differences in material thermal expansion during use must be accommodated. For example, if substrates for the DWA and CMOS are glass and silicon, respectively, the difference in thermal expansion coefficient will be ~$2 \times 10^{-6}$/° C. Across a 50 mm substrate with a 20° C. change in temperature, the thermal expansion mismatch between the two substrates is ~2 µm. This issue is addressed by the present invention by various strategies, including, but not limited to, use of a silicon DWA substrate, precise thermal expansion coefficient matching, and/or mechanical compliance.

Mechanical compliance of the contacts is a particularly desirable solution as it not only accommodates thermal expansion of the substrate but also addresses possible non-planarity of the contact arrays on both substrates. Compliance is a property of materials that may be expressed as the inverse of stiffness. Compliance may be achieved by several different methods or combinations of methods. In one embodiment, compliance is achieved by making the well contacts compliant, and thus able to compress to variable degrees under pressure and accommodate multiple different forces exerted upon them. This feature enables the plurality of well contacts of the DWA to form a plurality of electrical connections with the plurality of amplifier contacts in the CMOS array.

Figure 4A:
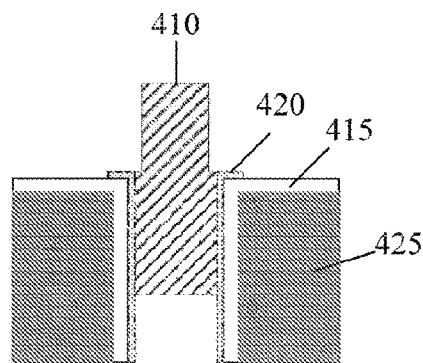
FIGS. 4A-C illustrate cross-sectional views of alternative embodiments of compliant connectors of the invention.

In one embodiment, as illustrated in FIG. 4A, compliant well contacts 410 are composed of an electrically conductive compliant polymer, e.g., poly(3,4-ethylenedioxythiophene) (PEDOT). In other embodiments, the compliant conductive material may be a hybrid polymer comprising conductive material, e.g., poly(3,4-ethylenedioxythiophene):polystyrene sulfonate (PEDOT:PSS). In another embodiment, the compliant conductive material is made from a non-conductive polymer mixed with a conductive powder, such as carbon nanotubes or gold nanobeads (see for example Unger, M. A., Chou, H.-P., Thorsen, T., Scherer, A. & Quake, S. R. Monolithic Microfabricated Valves and Pumps by Multilayer Soft Lithography. Science 288, 113-116 (2000)). The skilled artisan will appreciate that other compliant conductive polymers may be suitable for the practice of the present invention. Fabrication of the conductive compliant polymeric well contacts on silicon substrate 425 coated with oxide layer 415 and conductive seed layer 420 is discussed further with reference to FIGS. 4 and 5.

Figure 4B:
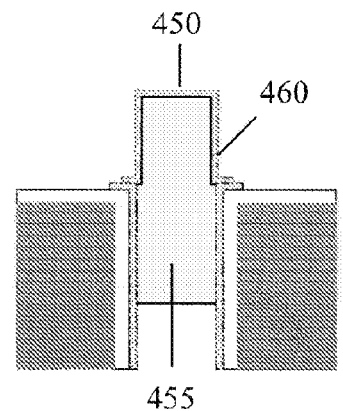

In another embodiment, illustrated in FIG. 4B, compliant contacts 450 are substantially formed by a compliant, but insulating, elastomer bump 455, composed of, e.g., polydimethylsiloxane (PDMS) with a thin ductile metal coating 460, making contact between the well electrode and top surface of the bump (see for example Aggarwal, A. O., Raj, P. M. & Tummala, R. R. High aspect ratio metal-polymer composite structures for nano interconnects. 9th International Symposium on Advanced Packaging Materials: Processes, Properties and Interfaces 182-186 (2004)).

In another embodiment, the compliant well contact is formed from a thin, bent beam of metal connected at one end to the surface adjacent to and in electrical contact with each DWA electrode opening. This beam acts as a spring, with any deflection from its initial position providing the force needed to keep the beam in contact with the CMOS array amplifier contacts (see for example Muthukumar, S. et al. High-density compliant die-package interconnects. in 56th Electronic Components and Technology Conference 2006 (2006)). The beam may be comprised of one or more metals, allowing for tuning of the stiffness of the beam (see for example Arunasalam, P., Ackler, H. D. & Sammakia, B. G. Microfabrication of ultrahigh density wafer-level thin film compliant interconnects for through-silicon-via based chip stacks. Journal of Vacuum Science & Technology B: Microelectronics and Nanometer Structures Processing, Measurement, and Phenomena 24, 1780-1784 (2006)).

The resultant electrical interconnection between the compliant well contacts and the CMOS amplifier contacts of the nanopore-based molecular analysis system is sufficient for detection of electrical signals generated in a majority of the plurality of wells of the DWA. However, one advantage of the systems of the present invention is that it is not necessary for electrical interconnection to be established between each of the plurality of wells and each of the plurality of amplifiers, as each well of the DWA functions as an independent sensor. Therefore, a certain degree of failed interconnection may be tolerated (e.g. 5% interconnect failure). As discussed herein, another advantage to the system is that the interconnections are temporary in nature, e.g., the connections can be broken at the end of the DWA lifespan, whereupon the DWA may be disposed and replaced with a fresh DWA on the original CMOS amplifier array.

With continued reference to FIG. 3, reusable CMOS amplifier array 310 of the nanopore molecular analysis system of the present invention may include any suitable complementary metal oxide semiconductor chips known in the art. The incorporation of semiconductors such as silicon into the devices provides for the inclusion of electronic circuitry in close association with the DWA. For example, the use of silicon allows for a multiplex device having an array of electronic circuits wherein each well in the DWA is directly associated with a set of electronic circuits. These circuits can provide the functions of measurement, data manipulation, data storage, and data transfer. The circuits can provide amplification, analog to digital conversion, signal processing, memory, and data output, and the like. A specialized adaptation of the CMOS amplifier device are features enabling the DWA intermediary substrate to be aligned so that the DWA electrodes are in correct position over the CMOS amplifier array contacts. In one embodiment, these features are photodiode arrays, which determine the DWA intermediary substrate position via holes fabricated through the DWA chip, through which light is passed. In another embodiment, these alignment features are simple electrical sensors, which mate with pairs of compliant electrodes on the DWA intermediary substrate, which are themselves electrically shorted, so that a complete electrical circuit is made when the DWA intermediary substrate compliant electrodes are properly positioned over the CMOS amplifier array connectors.

In a related embodiment, capacitive sensors are used to determine the alignment and overlap of the electrodes of the DWA chip and the connectors of the CMOS amplifier array. In another embodiment, the capacitance of the well electrodes themselves provide transient electrical signals measured by the CMOS amplifier array. The pattern of signals provided by the CMOS amplifier array shows which wells are in electrical contact, and allows determination of the orientation of the DWA chip, and from this, alignment can be perfected.

In another embodiment, the CMOS amplifier array connectors are designed to be recessed slightly below the general plane of the CMOS amplifier array, and the mechanical resistance to motion when the compliant electrode pillars drop into the recessed CMOS amplifier array connectors is used to promote proper alignment of the DWA intermediary substrate to the CMOS amplifier array.

In another embodiment, the DWA intermediary substrate and the CMOS amplifier array are moved to known, separate positions on a specifically designed instrument, with the position of each being determined by optical registration of markings on the surface of each device. Once in these known positions, the DWA intermediary substrate and the CMOS amplifier array are very precisely brought together, so that the compliant electrodes are properly positioned over the CMOS electrical connections. Any of the described alignment methods may also be used in combination, for example the optical detection of CMOS amplifier array to DWA intermediary substrate position used for initial alignment, and then the photodiode detection of light passing through specific holes on the DWA intermediary substrate used for final alignment.

Attachment of the DWA intermediary substrate 350 to the CMOS amplifier array 310 after alignment may be accomplished by a number of methods. In one embodiment, a thermally activated polymer on portions of the CMOS amplifier array, being deformable when above its activation temperature, may be used to reversibly bond the DWA intermediary substrate to the CMOS amplifier array. In another embodiment, vacuum force can be used to attach the DWA intermediary substrate reversibly to the CMOS amplifier array. In this embodiment, a gasket of pliant material is patterned on the interconnect-side of the DWA intermediary substrate to define the vacuum connection area. Inside this gasket region, one or more through-wafer holes similar to those of the DWA are created to provide vacuum access through the DWA intermediary substrate.

In most embodiments, the flow cell and DWA are integrated as a single disposable unit. Flow cell 380 of the nanopore molecular analysis system of the present invention supports the microfluidic processes of the system and has a flow cell channel that is an upper fluidic region in fluidic communication with the DWA. This upper fluidic region is located on the cis side of the nanopores disposed in each well, through which the molecules to be detected for sequence determination will pass. In some cases, the fluid regions on either side of the nanopore are referred to as the cis and trans regions, where the molecule to be measured generally travels from the cis region to the trans region through the nanopore. For the purposes of description, terms upper and lower are sometimes used to describe such reservoirs and fluid regions. It is to be understood that the terms upper and lower are used as relative rather than absolute terms, and in some cases, the upper and lower regions may be in the same plane of the device. The upper and lower fluidic regions are electrically connected either by direct contact, or by fluidic (ionic) contact with drive and measurement electrodes (i.e. counter and well electrodes, respectively). Methods for semiconductor and flow cell fabrication described herein and as known in the art can be employed to fabricate the devices of the invention.

Figure 5:
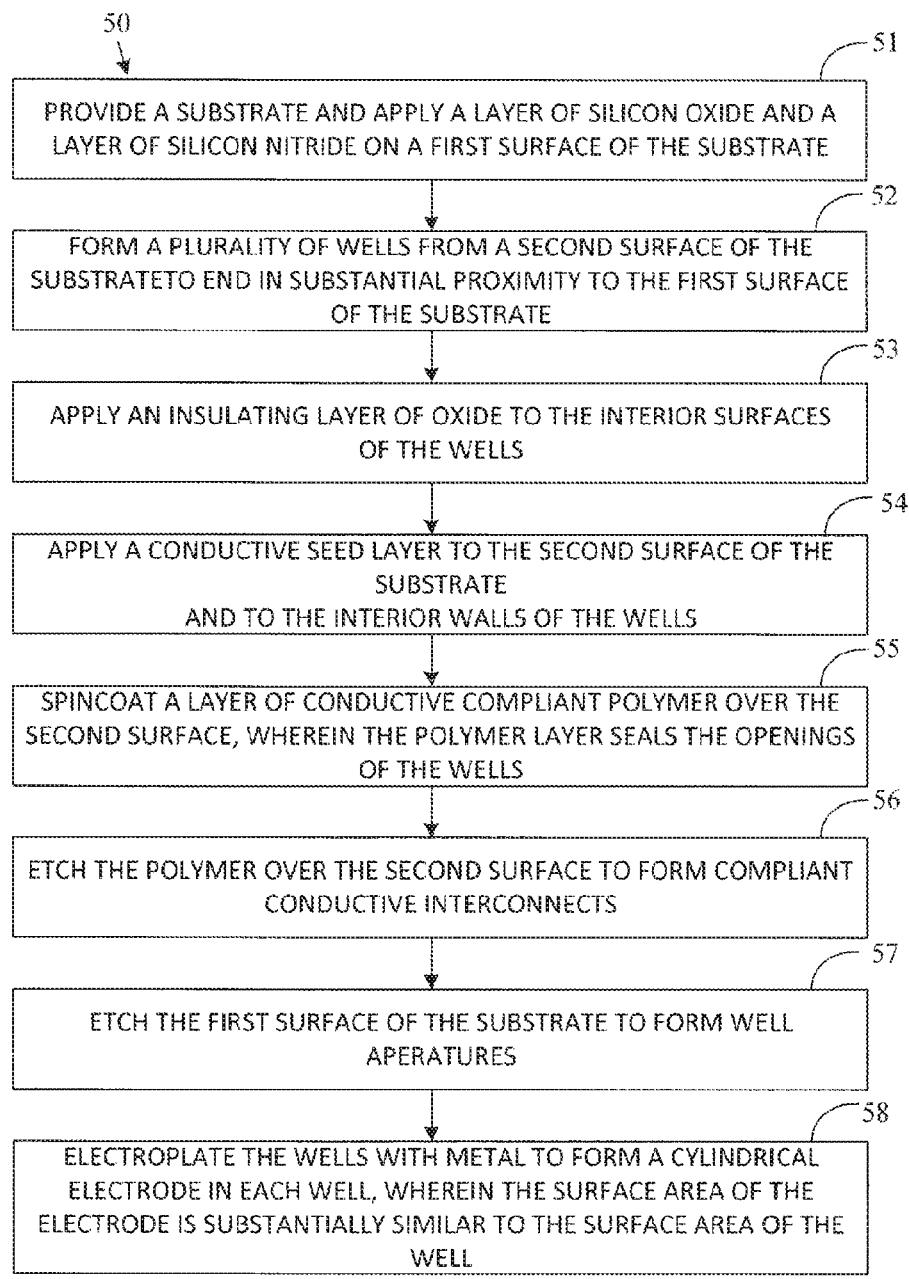
FIG. 5 is a flow diagram of a representative method of fabricating a disposable well array (DWA) of the invention.

FIG. 5 is a flow diagram of an exemplary method 50 for fabricating DWA 350, as illustrated in FIG. 3. In block 51 a substrate is provided, which in some embodiments may be a silicon wafer or chip with a thickness of around 300 μm, though substrates of any suitable thickness may be used. In a first step of the fabrication process of the present invention, a layer of material(s) is applied to a first surface of the substrate to function as an "etch stop" or a physical barrier that prevents subsequent etching from creating a hole entirely through the first surface. In preferred embodiments, the etch stop material is silicon oxide and/or silicon nitride. The etch stop material(s) may also provide the surface on which a lipid membrane is formed. In some embodiments, an additional material may be deposited on the first surface to modify the chemical functionality of the surface on which the lipid membrane is formed. This additional layer may be a fluorinated polymer, deposited by spin coating. In another embodiment, this layer may be a self-assembled monolayer of a silanization agent, which modifies the surface energy (see for example Smith, R. K., Lewis, P. A. & Weiss, P. S. Patterning self-assembled monolayers. Progress in Surface Science 75, 1-68 (2004)).

In block 52, a plurality of wells are formed in the substrate, spanning from the second surface to end in substantial proximity to the first surface of the substrate. In preferred embodiments, the wells extend through the entirety of the substrate and terminate at the layer(s) of etch stop material described with reference to block 51. The wells are herein referred to as "high aspect wells". In some embodiments, deep silicon etching is used to create high aspect wells, though several methods are suitable to create the arrays of wells of the present invention. Deep silicon etching typically refers to two methods, Bosch and cryogenic etching. Both of these processes can etch near vertical sidewalls and form hole arrays in silicon with aspect ratios (the ratio of the height of the well to the diameter of the well) of over 10. Through glass via research has demonstrated that similar hole arrays can be fabricated in thin glass, and in an alternative embodiment of the invention, glass may be used as the substrate. Using a glass substrate has the additional advantages of not requiring a process to electrically isolate the wells and the low cost of the raw substrate. As TSV technology is currently more developed, silicon substrates are the preferred embodiment, however it is to be recognized that the methods of this invention apply to other substrates.

In block 53, an insulating layer of silicon oxide is applied to the interior surfaces of the wells, and optionally, to the second surface of the substrate. In one embodiment, silicon oxide is thermally grown on the silicon substrate. In some embodiments, oxide may be grown at temperatures of around 800° C. to around 1200° C. with either a dry or wet oxidation environment. In alternative embodiments, low temperature chemical vapor deposition processes may be used to conformally deposit silicon oxides, such as TEOS. In another embodiment, the insulating layer may be aluminum oxide, deposited via atomic layer deposition. The capacitance of a well depends upon the insulating layer thickness. For example, a well with a diameter of 20 μm and a depth of 200 μm with a silicon oxide thickness of 0.5 μm can expect an incremental capacitance of ~0.7 pF. In nanopore current measurements, system capacitance greater than a few picoFarads (pF) can lead to significant noise at 10 kHz bandwidth or greater, so it is important to minimize this load. In one embodiment of the present invention, a 300 μm thick substrate with 20 μm diameter wells and a layer of applied silicon oxide of around 1 μm thick has a resultant capacitance of ~0.52 pF.

In block 54, a seed layer is applied to the second surface of the substrate and to the interior walls of the wells as a foundation layer to electroplate electrode material. Preferably, the seed layer is a conductive seed layer. This can be accomplished using a variety of techniques and metals developed for TSVs (see, e.g., T. Wei, J. Cai, Q. Wang, Y. Hu, L. Wang, Z. Liu, and Z. Wu, "Optimization and evaluation of sputtering barrier/seed layer in through silicon via for 3-D integration," Tsinghua Science and Technology, vol. 19, no. 2, pp. 150-160, 2014). During this step, is important to get continuous connectivity of the seed layer film down the well sidewall in order to get sufficient coverage of the electroplated electrode. Unlike TSVs, the seed layer for DWAs do not require continuity all the way through the length of the well, although deeper penetration is preferred, as the electroplated electrode (e.g. silver) only requires electrical connection up to the end of the well nearest the compliant electrical contacts. Electroplating the electrode metal is typically a final step in the DWA fabrication process, but electroplating may also be used to establish the seed layer.

In block 55, a layer of compliant conductive polymer is spincoated over the second surface, wherein the polymer seals the openings of the wells. In this step, formation of compliant connections is initiated. In one embodiment, a layer of around 10 μm of polymer is applied to the second surface.

In other embodiments, the sealing polymer is liquid impermeable and gas permeable. These properties are advantageous for DWAs designed for other applications. Polydimethylsiloxane (PDMS) is a common example of such a polymer.

In block 56, the polymer over the second surface is etched to form compliant conductive contacts, or "interconnects". In one embodiment, masks are first applied to the top and bottom surfaces, respectively, of the substrate to pattern the silicon nitride/oxide/seed layer and polymer/seed layer surfaces for etching.

In method 50 described above, the material of the compliant connector also acts as the seal of the end of the well, preventing liquid from travelling through the well and onto the CMOS amplifier array. In alternative methods of the invention, a well seal, or plug, is created prior to fabrication of the compliant conductive connectors. In these embodiments, the plug may be made of a similar or different material from the compliant conductor. The material may be non-conductive and provide a platform upon which a conductive interconnect is subsequently formed. The material may be spread over and partially into the wells via spin coating, spray coating, dip coating, doctor blading, or the like, and cured via thermal, optical, or other methods. After deposition, further processing, such as RIE, may be performed to limit this plug material to just the domain of the wells.

Another method of creating compliant well contacts is to seed a non-conductive, compliant polymer such as PDMS with low concentration of conductive particles such as carbon black or silver nanoparticles. At low doping levels (e.g., less than one percent), conductivity does not change significantly from the poor conductivity of the undoped polymer matrix. This material is spincoated over the DWA substrate processed as described in block 55. Alternative methods of thin film coating can be used, including spray-coating, dip coating, or squeegie-based methods. As further described in Example 1, PDMS can be coated over these hole arrays such that only a small amount of polymer flows into each well entrance. Before the polymer polymerizes, it is subjected to an electrical signal that aligns the conductive particles in the polymer matrix in conductive strings. This is accomplished by electrically connecting the DWA silicon substrate so it acts as an electrode under the substrate silicon oxide and spincoated polymer. Another planar electrode is applied to the top of the polymer so the gap between the two electrodes is the thickness of the silicon oxide plus the thickness of the polymer. Fields >500 V/cm applied at frequencies of ~10 Hz to 10 kHz are applied. Under these applied fields the conductive particles are dielectrophoretically driven to align in conductive strings between the electrodes, approximately along the field lines (see Knaapila, M., Hoyer, H., & Helgesen, G. Dielectrophoresis in particle confinement: Aligned carbon particles in polymer matrix below percolation threshold. The European Physical Journal Special Topics, 223(9), 1869-1882 (2014)). Because the silicon oxide and the well conductive coating are impenetrable to the particles, the conductive strings form between the polymer-side electrode and terminate on the oxide or the conductive liner in the wells. In this state, the polymer is crosslinked and the conductive strings are immobilized. This polymer film forms a highly anisotropic conductive film that will conduct between the well and the polymer surface directly above the well opening but is highly insulating between wells. A distinct advantage of this approach is that, due to this anisotropic conductivity, there would be no need for further patterning of this conductive sheet to electrically isolate the conductive pathway from each well, thus simplifying the fabrication process. Additionally, since there is conductivity over the entire extent of the DWA, the level of alignment accuracy between the DWA and the CMOS amplifier array to ensure electrical connectivity is, in some embodiments, reduced.

Another method to form contacts between the CMOS array and the corresponding DWA, which does not require patterning of the contact material after deposition, incorporates a film component that is sandwiched between the two contact arrays or, alternatively, is preattached to the DWA. This film should have an anisotropic conductivity that has very low lateral conductivity and be capable of forming electrical contact through its thickness. As previously described, a film with anisotropic conductivity does not require a high degree of lateral alignment, but rather just enough so that the area of the DWA overlays the area of the CMOS. One example of such a material is outlined by Maekawa, Y., Koshikawa, H., & Yoshida, M. Anisotropically conducting films consisting of sub-micron copper wires in the ion track membranes of poly(ethylene terephthalate). Polymer, 45(7), 2291-2295. (2004), which describes a method based on the use of track-etched polymer films. These are films, nominally tens of microns thick, which have random, directional, sub-micron diameter pores passing through the film thickness. The pores are electrolytically filled with a conductor such as copper. By controlling the surface finish, the resulting films conduct across their thickness but are laterally insulative. Track-etched polymer films are available commercially from a number of vendors (e.g. IT4IP, Belgium) in a variety of polymers. In one embodiment, electrolytic wires are formed using films with narrow pores at a density just sufficient for reliable electrical connection given the contact areas of each array element. Following this strategy, the resulting thin pore wires do not overly limit the compressibility of the anisotropically conductive film. To ensure a compliant interconnect, a flexible polymer, such as PDMS, may be chosen. Alternatively, a less compressible polymer, such as polycarbonate, could be chosen. In the device assembly process, this polymer may be heated to its softening point, so that it becomes compliant through plastic flow. For example, a typical polycarbonate has a softening point at 150° C. and will deform under low pressure.

Figure 4C:
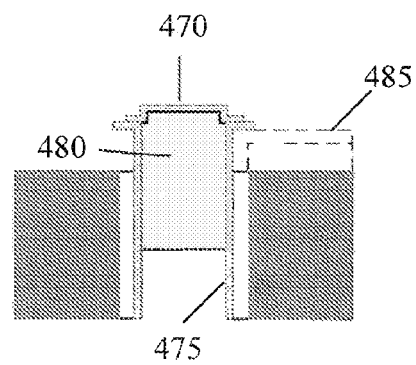

Another method of producing a DWA with compliant electrodes 470 as depicted in FIG. 4C begins with the well array, which has a thin continuous conductive coating 475 in the well and around the well entrance on the wafer surface. A polymer precursor 480 such as PDMS monomer is applied to form a thin film over the well array such that the material penetrates into each well a short distance and polymerizes. This distance can be controlled to be in the range of 5 to 100 microns deep. In one embodiment, residual polymer between the wells is etched away. A patterned metallization coats the polymer surface and contacts the conductive coating on the wafer surface intermittently along the well edges. At the next stage, the silicon substrate 485 (denoted in FIG. 4C by the hatch marks) is etched down using a silicon specific isotropic etch to preserve the polymer and the metallization. Xenon difluoride gas etching provides this functionality. The isotropic etch means the etchant can remove silicon through the intermittent openings along the well edge and can further etch laterally under the metal. After etching down multiple microns of silicon, a pillar array of metallized compliant polymer with coplanar tops is left standing. Each pillar has a metal top that forms electrical contact with its corresponding metalized well wall.

In block 57, the first surface is etched to form well apertures. It is not obligatory to the invention that the etching steps be performed in this sequential manner, and in alternative embodiments, the first and second surfaces are etched in the reverse order or at the same time. The diameter of the aperture in the first surface may be the same or smaller than the well diameter.

In block 58, the wells are electroplated with metal to form cylindrical electrodes in each well, wherein the surface area of the electrode is substantially similar to the surface area of the well. In one embodiment, the electrode material is grown radially in from the well wall. Growing the electrode cylindrically from wall of the high aspect cylindrical well in DWAs increases electrode surface area, which lowers the current density and increases the limiting thickness of AgCl, as described above. This leads to improved conductivity and longer operational lifespan.

FIGS. 6A-H illustrate one embodiment of the fabrication process of the present invention. It is to be understood that many processes and techniques used to fabricate TSVs can be applied to the fabrication methods of the present invention. The following disclosure describes these steps generally.

Figure 6A:
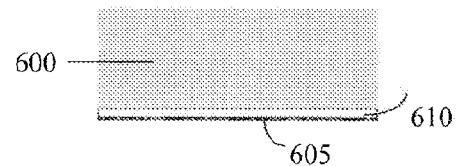
FIGS. 6A-H illustrate one embodiment of the method summarized in FIG. 5.

FIG. 6A illustrates substrate 600, which in some embodiments may be a silicon wafer or chip with a thickness of around 300 µm, though substrates of any suitable thickness may be used. In this embodiment, silicon oxide layer 610 and silicon nitride layer 605 are applied to a first surface of substrate 600.

Figure 6B:
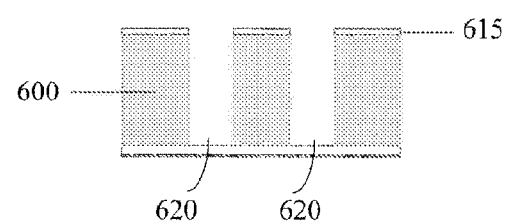

FIG. 6B illustrates high aspect wells 620 that have been etched into substrate 600. Further illustrated in FIG. 6B is mask 615 that is used to pattern the via (i.e. well) arrays with well diameters, e.g., of 20 µm. In this embodiment, the high aspect wells extend through the substrate and end at the first surface of the substrate, though other suitable well depths are contemplated by the present invention.

Figure 6C:
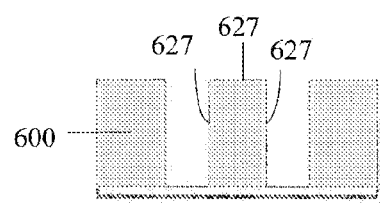

FIG. 6C illustrates substrate 600 with wells that are electrically isolated from the substrate and each other by insulating coating 627.

Figure 6D:
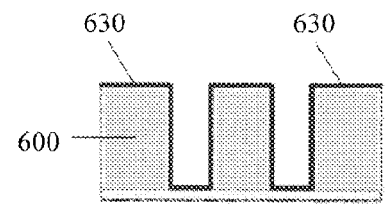

FIG. 6D illustrates substrate 600 deposited with seed film 630.

Figure 6E:
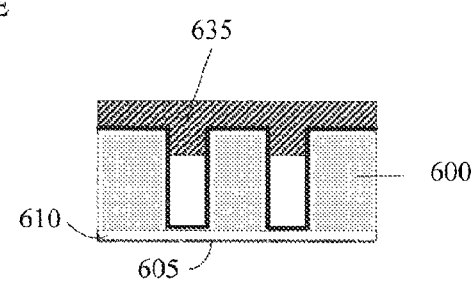

FIG. 6E illustrates substrate 600 with wells partially filled and sealed with compliant conductive polymer 635.

Figure 6F:
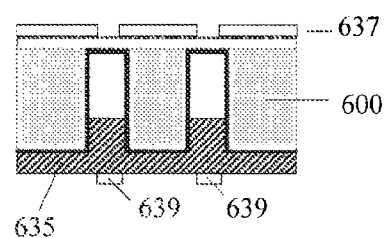
Figure 6G:
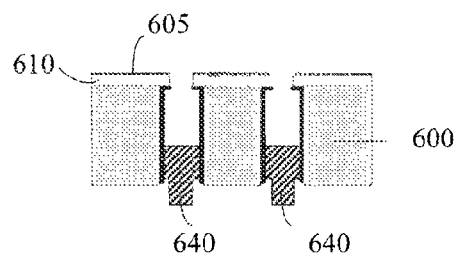

FIG. 6F illustrates substrate 600 in an inverted configuration with compliant conductive polymer 635 positioned on the bottom of the array. Masks 637 and 639 are applied to the first and second surfaces, respectively, of the substrate to pattern the silicon nitride/oxide/seed film and polymer/seed surfaces for etching. FIG. 6G illustrates substrate 600 with the silicon oxide 610 and silicon nitride 605 surface etched to create well apertures and polymer/seed surface etched to create conductive compliant polymeric pillars 640 (i.e. interconnects) at the bottom of each well of the DWA.

Figure 6H:
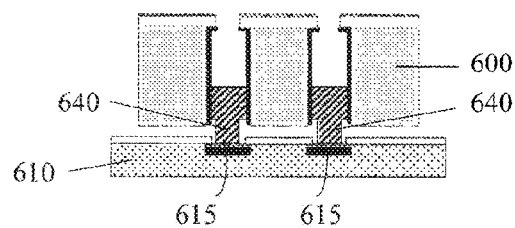

FIG. 6H illustrates substrate (i.e. well array) 600 with compliant conductive interconnects (i.e. contact array) 640 each aligned with a cohort amplifier 615 on CMOS electrode array 610.

EXAMPLES

Example One

Fabrication of a Dense Array of High Aspect Nanoscale Wells Sealed with Compliant Plugs This example demonstrates fabrication of a modified substrate that provides a platform for the fabrication of several DWAs of the present invention. The substrate is modified by creating a dense array of high aspect wells on one surface that are subsequently sealed with mechanically compliant polymeric plugs with an overlaying surface layer. This is the first step towards creating compliant, conductive contacts over or adjacent to the wells.

Figure 7:
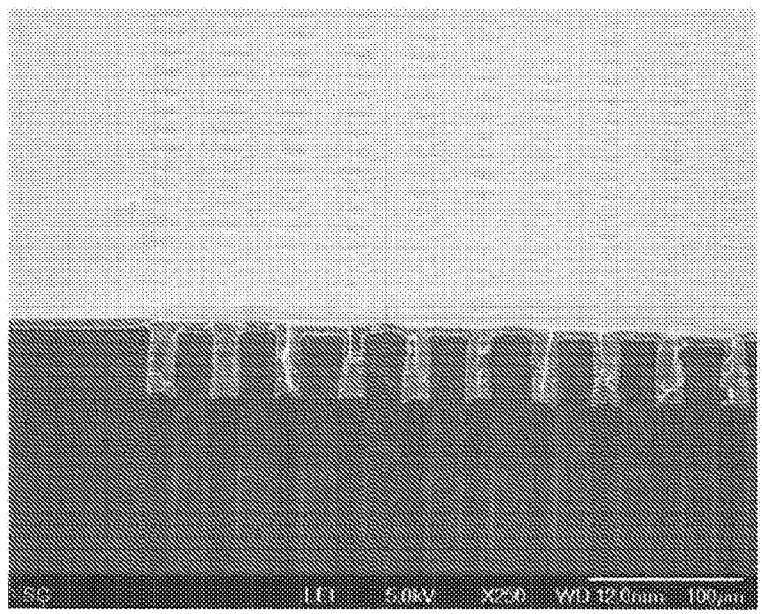
FIG. 7 is a SEM image showing a cross-sectional view of an array of plugged microwells.

The starting substrate was a 500 µm thick silicon wafer with a <100> crystallographic orientation. The substrate was patterned with photoresist to define the mask pattern of a dense array of 20 micron diameter wells. A Bosch deep reactive ion etch (DRIE) process was then used to etch wells in the substrate with a depth of approximately 160 µm. The density of the resultant deep wells was 62,500 wells per cm$^2$. To electrically isolate the wells from each other, a layer of silicon oxide was thermally grown in the wells to a suitable thickness. As an initial step to form compliant conductive interconnects, polydimethylsiloxane (PDMS), commercially available as SYLGARD 184, was prepared by mixing the catalyst and precursor in a ratio of 1:10. The mixture was spun coat over the wafer substrate and thermally cured in place to "plug" the open end of the wells. The wafer substrate was then cleaved through the well array, and a cross-sectional image was taken using a scanning electron microscope (SEM) to observe the extent of plug formation. The image in FIG. 7 shows the PDMS layer (the regions of lighter shade), approximately 7 um thick, coating the silicon substrate and completely sealing each well in the array (the regions of darker shade). The PDMS penetrates approximately 45 µm into the well cavities.

The development of a process to efficiently form dense arrays of wells that are sealed with plugs of compliant polymer provides a critical foundation for further methods described herein, e.g., for the fabrication of DWAs with compliant conductive contacts that enables electrical coupling of the well electrode to a CMOS sensor for nanopore-based molecular analysis applications. For example, compliant conductive contacts may be constructed from either a conductive polymer or a non-conductive polymer by etching pillars from the polymeric layer on the surface of the substrate described in this Example. In the latter case the polymeric pillars are coated with a thin metal layer to make the electrical contacts. Alternatively, the wells are sealed with plugs of PDMS, as described above, and metal spring connectors or compliant metallized polymeric pillars are subsequently fabricated adjacent to, or on top of, the plugs.

Example Two

Fabrication of a Dense Array of High Aspect Nanoscale Wells with Compliant Pillar Interconnects This example demonstrates fabrication of a dense array of high aspect wells with compliant pillar interconnects for forming electrical connections with a separate CMOS module. Once the lifespan of the DWA has expired, the temporary nature of the interconnects enables it to be removed and replaced with a fresh DWA. Thus the valuable CMOS module may, advantageously, be retained and reused.

Figure 8:
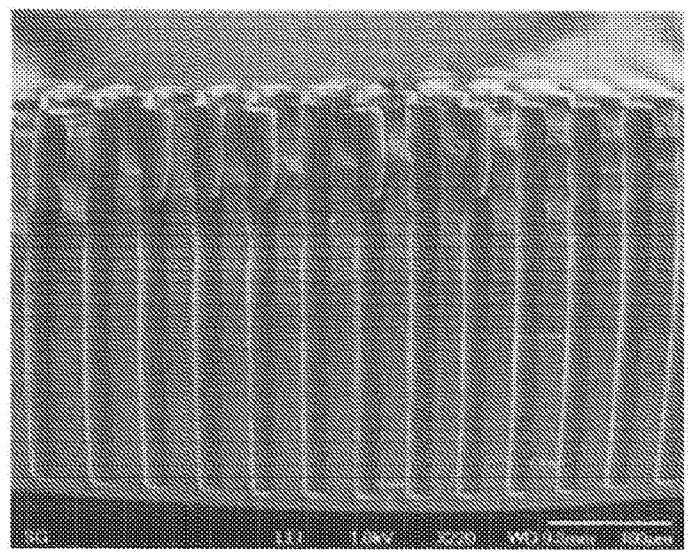
FIG. 8 is a SEM image showing a cross-sectional view of an array of plugged microwells with adjacent compliant pillars.
Figure 9:
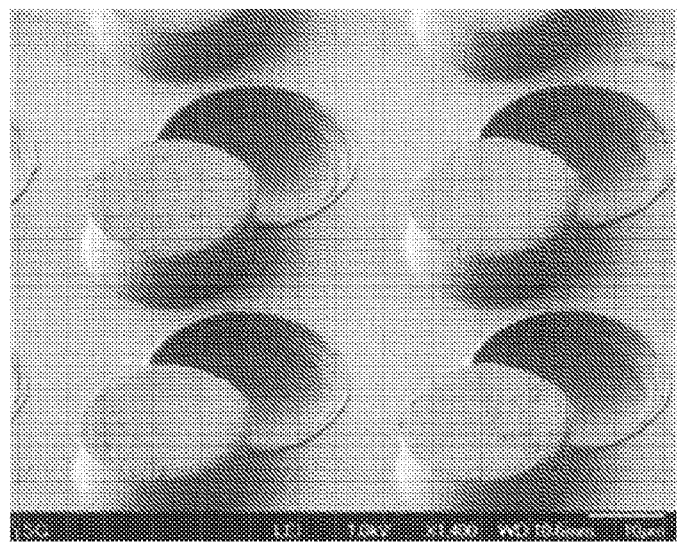
FIG. 9 is a SEM image showing a top view of the array of FIG. 8 with increased magnification.
Figure 10:
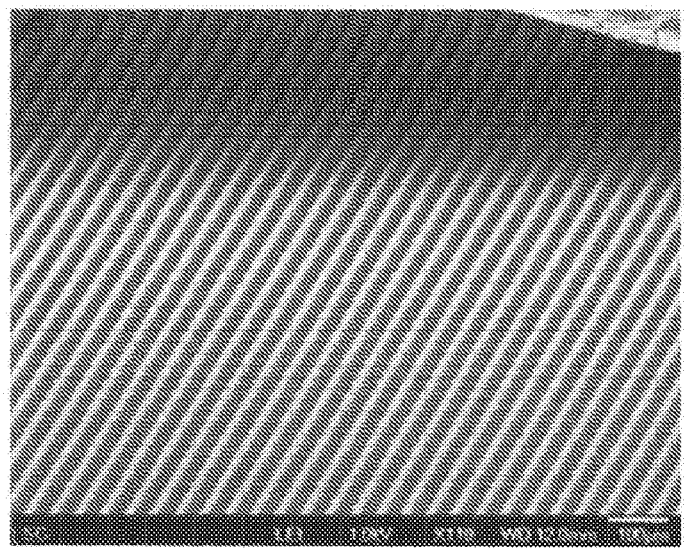
FIG. 10 is a SEM image showing a top view of the array of FIG. 8 with decreased magnification.

In this experiment, the starting substrate was a 300 µm thick silicon wafer. The first side of the substrate was coated with silicon oxide by plasma enhanced chemical vapor deposition (PECVD) deposition. The second side was patterned with photoresist to define the pattern of a dense array of wells. A Bosch DRIE process was then used to etch deep wells in the substrate to within 10 µm of the first side of the wafer. These wells were 20 um in diameter spaced at 40 um intervals, advantageously resulting in an areal density of 62,500 wells per cm$^2$. After removing the photoresist, an electrically insulating layer of silicon oxide was thermally grown in the wells to a thickness of about 25 nm. A layer of aluminum was then deposited on the second side of the wafer to act as an etch stop layer and protect the top of the silicon surface during subsequent etching. A layer of PDMS was applied to the second surface by spin coating and thermal curing to create layer approximately 2.5 µm deep over the entire surface. A blanket reactive ion etch (ME) was used to remove the PDMS that lay above the second surface of the wafer, while leaving the PDMS plugs in the wells. The aluminum layer was then removed and a thick layer of photoresist was deposited and patterned on the second surface of the wafer with patterned voids in the resist to define regions in which compliant pillars would form. A second layer of PDMS was applied over the photoresist by spin coating, filling in the resist voids and leaving an approximately four μm thick blanket film over the 12 μm thick photoresist. A blanket RIE etch was used to remove the PDMS to the surface of the photoresist. The photoresist was then removed by a solvent soak, leaving compliant pillars on the surface. The wafer was cleaved into sections running through the dense well arrays, which were imaged using a scanning electron microscope. A cross-sectional image is presented in FIG. 8, which shows the PDMS plugs completely sealing each well in the array, with adjacent pillars observed on the surface of the substrate. The image presented in FIG. 9 offers a higher magnification top view, showing details of the alignment of pillars and plugged wells. The image in FIG. 10 is a lower magnification top view, showing the dense array of pillars and corresponding wells. This alternative method of adding PDMS pillars adjacent to the wells using a second PDMS coating can provide additional dimensional control at the cost of additional process complexity.

Example Three

Description of Complete DWA Fabrication Process

In this exemplary process, the starting substrate is a 300 um thick, 300 mm diameter silicon wafer. The first side is coated with silicon oxide and silicon nitride. The second side is patterned with photoresist to define the dense array of wells. These wells are etched through the wafer using a Bosch DRIE process, stopping at the silicon oxide layer of the front surface. An insulating layer of silicon oxide is grown inside the wells, and on the second surface of the wafer, by thermal oxidation. A thin, conductive seed layer of metal is conformally deposited on all surfaces of the wells, as well as the second side of the wafer, by atomic layer deposition. A thin layer of PDMS is applied to the second surface by spin coating, flowing partway into the wells to form plugs before being thermally cured. A RIE process removes the PDMS above the plane of the second surface, leaving PDMS plugs with the top surfaces nearly coplanar with the top surface of the second side, and also exposing the seed metal layer on the second side surface. A layer of photoresist is patterned on the second side, to define voids that define the size and height of the compliant pillar interconnects. A layer of PDMS is applied over the photoresist by spin coating, and thermally cured in place. This layer of PDMS is removed by RIE until the top of the resist layer is exposed. The resist layer is then removed, leaving the compliant pillars free-standing. A thin layer of conductive, ductile metal is conformally deposited on the second surface by sputter deposition. A layer of photoresist is patterned on top of this ductile metal layer, leaving resist over the conductive pillars and a 1 μm ring around each pillar. The ductile metal layer and conductive seed layer of metal are removed by wet chemical etching, leaving those areas protected by photoresist; i.e. the compliant pillars covered with metal which makes connection to the seed layer around the base of each pillar. A layer of photoresist is applied to the first surface and patterned to define the openings to each well in the DWA on the first surface. By RIE etching, the silicon nitride, oxide, and seed metal layer are penetrated to give access to each well cavity. Each of the numerous chips fabricated in this batch process on the wafer is separated by dicing and each chip is integrated into a microfluidic cell.

Example Four

Process to Align and Attach Dense Well Array Chip to CMOS Amplifier Array

This example describes how a disposable DWA can be aligned to a CMOS amplifier array chip so that each well contacts a single CMOS amplifier with no overlap. There are several methods by which the dense well array chip (DWA) may be aligned to the CMOS amplifier array and attached, so that the compliant well interconnects are in electrical connection with the CMOS amplifier contact pads. In this example, a multi-axis actuator is used to align and contact the DWA to the CMOS chip, and vacuum pressure is used to reversibly connect the devices.

The CMOS amplifier array is positionally fixed on the instrument, with permanent electrical connections made to external control and recording equipment. The DWA chip is attached to a 4-axis stage that can translate in x, y, and z directions and rotate about the z-axis. The x and y axes are coplanar with the DWA surface as it sits on the stage and is nominally pre-aligned parallel with the CMOS surface. Via an optical microscope, the DWA chip is brought into nominal coarse alignment in the x and y plane at a known distance in z above the CMOS chip—using a precise visible mark on the first (top, opposite to compliant interconnection array) surface of the DWA.

For fine alignment, two special wells, on opposite corners of the DWA, are fabricated during the DWA fabrication process. These wells are unique in that there is no metal over the compliant, optically clear polymer material of the interconnect (such as PDMS), so that light can pass through the well. Intense LED light is shone onto the front of the DWA over each of these wells, passing down the well, through the compliant plug/pillar at the end of the well, and onto the surface of the CMOS chip. On the CMOS chip, corresponding to the area in which these light-pipe wells will be located at perfect alignment, are placed arrays of photodetectors. The Lambertian distribution of light from this well is used by the photodetector array to determine the position of the DWA over the CMOS.

Lastly, the chip is lowered using the z-motion positioner until the DWA array comes into contact with the chip; this can be accomplished by mounting the DWA chip on the positioner arm with a connection that does not apply a force in the plus-z direction (such as tray, precision cut to the size of the DWA chips).

A strong, temporary connection between the DWA and the CMOS chip is accomplished via vacuum, by appropriate placement of ports and gaskets. Once the lifetime of a particular DWA has been extinguished, the removal of the vacuum pressure will release the DWA from the CMOS chip, and the precision positioner device may be used to remove it away from the CMOS chip, to a convenient position for the old DWA chip to be removed from the device, and a new chip added.

All of the U.S. patents, U.S. patent application publications, U.S. patent applications, foreign patents, foreign patent applications and non-patent publications referred to in this specification are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application.

Nothing herein is to be construed as an admission that the inventors are not entitled to antedate any referenced publication by virtue of prior invention.

What is claimed is:

1. A high density array of microwells, the array comprising:
   a) a substrate, wherein the substrate comprises a plurality of microwells, wherein the dimension of each of the microwells is defined by a high aspect ratio, and wherein the substrate is comprised of silicon or glass;
   b) a plurality of electrodes, wherein a single electrode is disposed in each of the plurality of microwells; and
   c) a plurality of connectors, wherein each of the connectors is in electrical communication with a microwell.

2. The high density array of claim 1, wherein the high aspect ratio is greater than or equal to a height to diameter ratio of about 5.

3. The high density array of claim 1, wherein the high aspect ratio is greater than or equal to a height to diameter ratio of about 10.

4. The high density array of claim 1, wherein the high aspect ratio is greater than or equal to a height to diameter ratio of about 15.

5. The high density array of claim 1, wherein the substrate has a thickness of about 300 µm and each of the microwells has a diameter of about 20 µm and a depth of up to about 300 µm.

6. The high density array of claim 1, wherein each of the plurality of electrodes has a surface area that covers greater than 25 percent of the interior walls of the microwell in which it is disposed.

7. The high density array of claim 1, wherein each of the plurality of electrodes has a surface area that covers great than 50 percent of the interior walls of the microwell in which it is disposed.

8. The high density array of claim 1, wherein each of the plurality of electrodes has a surface area that covers substantially 100 percent of the interior walls of the microwell in which it is disposed.

9. The high density array of claim 1, wherein the density of the microwells is greater than about 10,000 per $cm^2$.

10. The high density array of claim 1, wherein the density of the microwells is greater than about 50,000 per $cm^2$.

11. The high density array of claim 1, wherein each of the connectors is compliant.

12. The high density array of claim 11, wherein each of the compliant connectors is comprised of a non-conductive compliant polymer coated with a metal.

13. The high density array of claim 11, wherein the compliant connectors are comprised of a conductive compliant polymer.

14. A device for determining nucleic acid sequence information, the device comprising:
   a) a high density array of microwells of claim 1;
   b) a semiconductor chip in reversible electrical communication with the high density array; and
   c) an upper fluidic region in fluidic communication with the high density array.

15. The device of claim 14, wherein the high density array and the upper fluidic region are disposable and the semiconductor chip is reusable.

16. The device of claim 14, wherein one or more of the connectors of the array are compliant and form the electrical communication with the semiconductor chip.

17. The device of claim 16, wherein the compliant connectors comprise a PEDOT polymer or a hybrid polymer comprising a conductive material.

18. The device of claim 16, wherein the compliant connectors comprise a non-conductive polymer coated with a metal.

19. A high density array of microwells, the array comprising:
   a) a substrate, wherein the substrate comprises a plurality of microwells, wherein the dimension of each of the microwells is defined by a high aspect ratio;
   b) a plurality of electrodes, wherein a single electrode is disposed in each of the plurality of microwells; and
   c) a plurality of connectors, wherein each of the connectors is in electrical communication with a microwell, and wherein each of the connectors is compliant.

20. The high density array of claim 19, wherein each of the compliant connectors is comprised of a non-conductive compliant polymer coated with a metal.

21. The high density array of claim 19, wherein the compliant connectors are comprised of a conductive compliant polymer.

22. A device for determining nucleic acid sequence information, the device comprising:
   a) a high density array of microwells of claim 19;
   b) a semiconductor chip in reversible electrical communication with the high density array; and
   c) an upper fluidic region in fluidic communication with the high density array.

23. The device of claim 22, wherein the high density array and the upper fluidic region are disposable and the semiconductor chip is reusable.

24. The device of claim 22, wherein the compliant connectors comprise a PEDOT polymer or a hybrid polymer comprising a conductive material.

25. The device of claim 22, wherein the compliant connectors comprise a non-conductive polymer coated with a metal.

* * * * *